US00PP17492P2

(12) United States Plant Patent
Bergman

(10) Patent No.: US PP17,492 P2
(45) Date of Patent: Mar. 13, 2007

(54) ***HIBISCUS* PLANT NAMED 'BELIZE BREEZE'**

(50) Latin Name: *Hibiscus rosa-sinensis*
Varietal Denomination: Belize Breeze

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 22 days.

(21) Appl. No.: 11/177,953

(22) Filed: Jul. 8, 2005

(51) Int. Cl.
*A01H 5/00* (2006.01)

(52) U.S. Cl. ..... Plt./257

(58) Field of Classification Search ..... Plt./257
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct *Hibiscus* plant named 'Belize Breeze', characterized by its compact, upright, outwardly spreading, uniform, dense and symmetrical plant habit that is appropriate for container production; glossy and dark green-colored leaves; uniform and freely flowering habit; pink-colored flowers with white centers; good resistance to flower bud abscission during shipping; and tolerance to pathogens common to *Hibiscus* grown under Florida production conditions.

2 Drawing Sheets

Botanical designation: *Hibiscus rosa-sinensis.*
Cultivar denomination: 'Belize Breeze'.

BACKGROUND OF THE INVENTION

The present invention relates to a new and distinct cultivar of *Hibiscus,* botanically known as *Hibiscus rosa-sinensis,* and hereinafter referred to by the name 'Belize Breeze'.

The new *Hibiscus* is a product of a planned breeding program conducted by the Inventor in Alva, Fla. The objective of the breeding program is to create new freely-branching *Hibiscus* cultivars with a dense, uniform and compact plant habit appropriate for container production, early and uniform flowering, numerous flowers per lateral branch, desirable flower color and good postproduction longevity.

The new *Hibiscus* originated from a cross-pollination made by the Inventor in Alva, Fla. in late 1998, of a proprietary *Hibiscus rosa-sinensis* selection, designated as code number YB-1390, not patented, as the female, or seed, parent with the *Hibiscus rosa-sinensis* cultivar Kardinal Pink, not patented, as the male, or pollen, parent. The cultivar Belize Breeze was discovered and selected by the Inventor as a flowering plant within the progeny of the stated cross-pollination in a controlled environment in Alva, Fla., on Sep. 27, 2000.

Asexual reproduction of the new *Hibiscus* by vegetative terminal cuttings in a controlled environment in Alva, Fla. since February, 2001, has shown that the unique features of this new *Hibiscus* are stable and reproduced true to type in successive generations.

SUMMARY OF THE INVENTION

The cultivar Belize Breeze has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Belize Breeze'. These characteristics in combination distinguish 'Belize Breeze' as a new and distinct cultivar:

1. Upright, outwardly spreading, uniform, dense and symmetrical plant habit that is appropriate for container production.
2. Glossy, palmately-lobed and dark green-colored leaves.
3. Uniform and freely flowering habit.
4. Ruffled pink-colored flowers with white centers.
5. Good resistance to flower bud abscission during shipping.
6. Tolerant to pathogens common to *Hibiscus* grown under Florida production conditions.

Plants of the new *Hibiscus* can be compared to plants of the female parent, the proprietary *Hibiscus* selection code number YB-1390. Plants of the new *Hibiscus* differ from plants of the female parent selection in the following characteristics:

1. Plants of the new *Hibiscus* are not as vigorous as plants of the female parent selection.
2. Plants of the new *Hibiscus* have palmately-lobed foliage whereas plants of the female parent selection do not have lobed foliage.
3. Plants of the new *Hibiscus* and the female parent selection differ in flower color as plants of the female parent selection have lighter pink-colored flowers and pink centers.

Plants of the new *Hibiscus* can be compared to plants of the male parent, the cultivar Kardinal Pink. Plants of the new *Hibiscus* differ from plants of the cultivar Kardinal Pink in the following characteristics:

1. Plants of the new *Hibiscus* are not as vigorous as plants of the cultivar Kardinal Pink.
2. Plants of the new *Hibiscus* and the cultivar Kardinal Pink differ in flower color as plants of the cultivar Kardinal Pink have lighter pink-colored flowers with dark pink centers.

Plants of the new *Hibiscus* can be compared to plants of the *Hibiscus* cultivar Pink Versicolor, not patented. In side-by-side comparisons conducted in Alva, Fla., plants of the new *Hibiscus* differed from plants of the cultivar Pink Versicolor in the following characteristics:

1. Plants of the new *Hibiscus* were more freely flowering than plants of the cultivar Pink Versicolor.
2. Plants of the new *Hibiscus* and the cultivar Pink Versicolor different in flower color as plants of the cultivar Pink Versicolor had dark rose pink-colored flowers with dark pink centers.

BRIEF DESCRIPTION OF THE PHOTOGRAPHS

The accompanying colored photographs illustrate the overall appearance of the new *Hibiscus,* showing the colors as true as it is reasonably possible to obtain in colored reproductions of this type. Colors in the photographs may differ slightly from the color values cited in the detailed botanical description which accurately describe the colors of the new *Hibiscus.*

The photograph on the first sheet comprises a side perspective view of five typical flowering plants of 'Belize Breeze' grown in a container.

The photograph on the second sheet comprises a close-up view of a typical flower of 'Belize Breeze'.

DETAILED BOTANICAL DESCRIPTION

The photographs and following observations, measurements and values describe plants grown in Alva, Fla., with five plants per 16.5-cm container in polyethylene-covered greenhouses during the late summer under conditions which closely approximate commercial production. During the production of the plants, day temperatures ranged from 16 to 37° C. and night temperatures ranged from 13 to 26° C. Plants were about four months old when the photographs and the description were taken. In the description, color references are made to The Royal Horticultural Society Colour Chart, 1995 Edition, except where general terms of ordinary dictionary significance are used.

Botanical classification: *Hibiscus rosa-sinensis* cultivar Belize Breeze.

Parentage:

*Female or seed parent.*—Proprietary selection of *Hibiscus rosa-sinensis* designated as code number YB-1390, not patented.

*Male or pollen parent.*—*Hibiscus rosa-sinensis* cultivar Kardinal Pink, not patented.

Propagation:

*Type.*—By vegetative terminal cuttings.

*Time to initiate roots.*—About 10 days at temperatures of 24° C.

*Time to develop roots.*—About four weeks at temperatures of 24° C.

*Root description.*—Thick, fibrous; white in color.

*Rooting habit.*—Somewhat freely branching; moderately dense.

Plant description:

*Plant form and growth habit.*—Perennial, evergreen, upright, outwardly spreading, uniform, dense and symmetrical plant habit; inverted triangle. Moderately vigorous growth habit.

*Branching habit.*—Freely branching, usually about four lateral branches develop after removal of terminal apex.

*Plant height.*—About 27.5 cm.

*Plant diameter* (*area of spread*).—About 39 cm.

*Lateral branch description.*—Length: About 25 cm. Diameter: About 5 mm. Internode length: About 2 cm. Strength: Strong, but flexible. Texture: Immature, pubescent; mature, woody and rough. Color: Immature: Close to 146A. Mature: Close to 197A.

*Foliage description.*—Arrangement: Alternate, single; numerous; symmetrical. Length: About 7.5 cm. Width: About 7.8 cm. Shape: Ovate to cordate; palmately lobed. Apex: Acute; typically reflexed. Base: Cordate to obtuse. Margin: Palmately-lobed; crenate. Texture, upper surface: Smooth to sparsely pubescent; rough; leathery. Luster, upper surface: Glossy. Luster, lower surface: Somewhat glossy. Venation pattern: Palmate. Color: Developing and fully expanded foliage, upper surface: Darker green than 147A. Developing and fully expanded foliage, lower surface: Close to 147A. Venation, upper surface: 147A to darker green than 147A. Venation, lower surface: Close to 147A to darker green than 146A. Petiole: Length: About 3.5 cm. Diameter: About 2.5 mm. Texture, upper and lower surfaces: Pubescent. Color, upper surface: Close to 147A. Color, lower surface: Close to 146A to 147A.

Flower description:

*Flower arrangement.*—Flowers arranged singly at terminal leaf axils. Freely flowering with usually about three to four flower buds and/or open flowers per terminal apex. Flowers face upright to outwardly.

*Flower appearance.*—Rounded, pink-colored flowers with white centers. Flowers are open for about one to two days. Flowers persistent.

*Fragrance.*—None detected.

*Natural flowering season.*—Usually spring and summer or during periods of warm weather.

*Flower bud* (*before stage of showing color*).—Resistance to abscission during shipping: Plants of the new *Hibiscus* have been observed to resist flower bud drop when stored in a closed box for 5 days at 13° C. Length: About 2.25 cm. Diameter: About 1.2 cm. Shape: Ovoid. Color: Close to 146A.

*Flower diameter.*—About 9.7 cm.

*Flower length* (*height*).—About 7.25 cm.

*Petals.*—Arrangement: Corolla consists of five petals that are fused at base; petals imbricate. Length: About 6.6 cm. Width: About 5.2 cm. Shape: Roughly obovate to spatulate. Apex: Rounded. Base: Attenuate. Margin: Entire; ruffled. Texture, upper and lower surfaces: Smooth, glabrous, satiny; center, waxy. Color: When opening and fully opened, upper surface: Close to 65A; center, close to 155D. When opening and fully opened, lower surface: Close to 65B to 65C.

*Sepals.*—Appearance: Five sepals fused into a tubular star-shaped calyx. Length: About 3 cm. Width: About 1 cm. Shape: Oblong. Apex: Cuspidate. Margin: Entire. Texture, upper surface: Smooth; waxy. Texture, lower surface: Sparsely pubescent. Color, upper surface: Close to 146B. Color, lower surface: Close to 146A.

*Flower bracts.*—Appearance: About eight fused at base. Length: About 1.7 cm. Width: About 5 mm.

Shape: Lanceolate. Apex: Sharply acute. Margin: Entire. Texture, upper surface: Smooth, glabrous. Texture, lower surface: Sparsely pubescent. Color, upper surface: Close to 146A. Color, lower surface: Close to 147A.

*Peduncles.*—Length: About 3.1 cm. Diameter: About 2.25 mm. Angle: Straight to slightly bent. Strength: Strong, flexible. Texture: Sparsely pubescent. Color: Close to 146A.

*Reproductive organs.*—Androecium: Stamen number: Numerous, about 50. Filament length: About 5 mm. Filament color: Close to 155D. Anther shape: Reniform. Anther size: About 2 mm by 1.5 mm. Anther color: Close to 4D. Amount of pollen: Abundant. Pollen color: Close to 12A. Gynoecium: Pistil length: About 6.5 cm. Style length: About 5.5 cm. Style texture: Smooth, waxy. Style color: Close to 155D. Stigma appearance: Five, rounded. Stigma color: Close to 12A. Ovary color: Close to 144A.

*Seed/fruit.*—Seed and fruit production has not been observed.

Temperature tolerance: Plants of the new *Hibiscus* have been observed to tolerate temperatures from 0 to 38° C.

Disease/pest tolerance: Plants of the new *Hibiscus* grown under Florida production conditions have shown to be relatively tolerant to pathogens common to *Hibiscus* such as Pseudomonas, Pythium and Phytophthora. Plants of the new *Hibiscus* have not been observed to be tolerant to pests and other pathogens.

It is claimed:

1. A new and distinct *Hibiscus* plant named 'Belize Breeze', as illustrated and described.

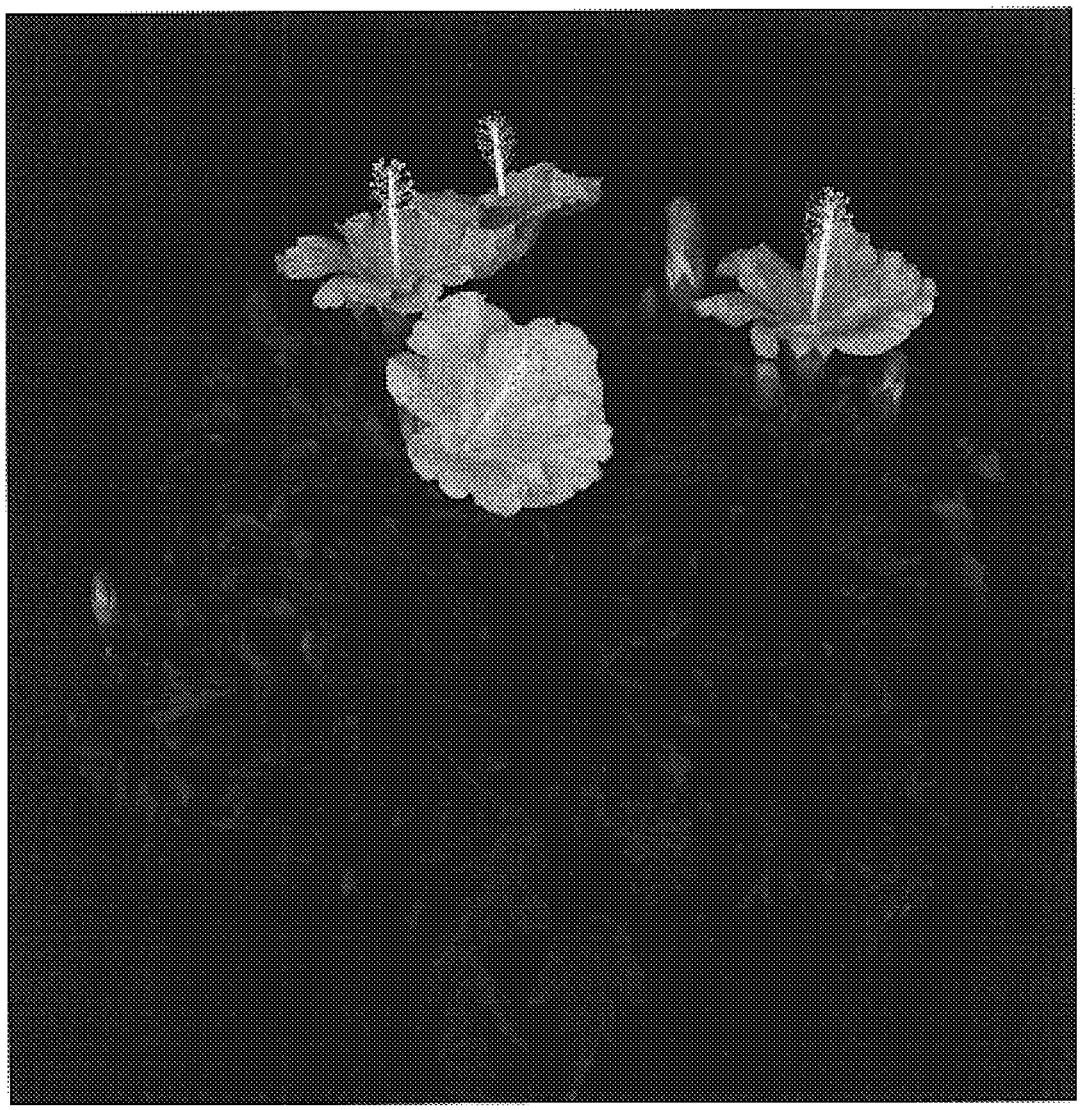

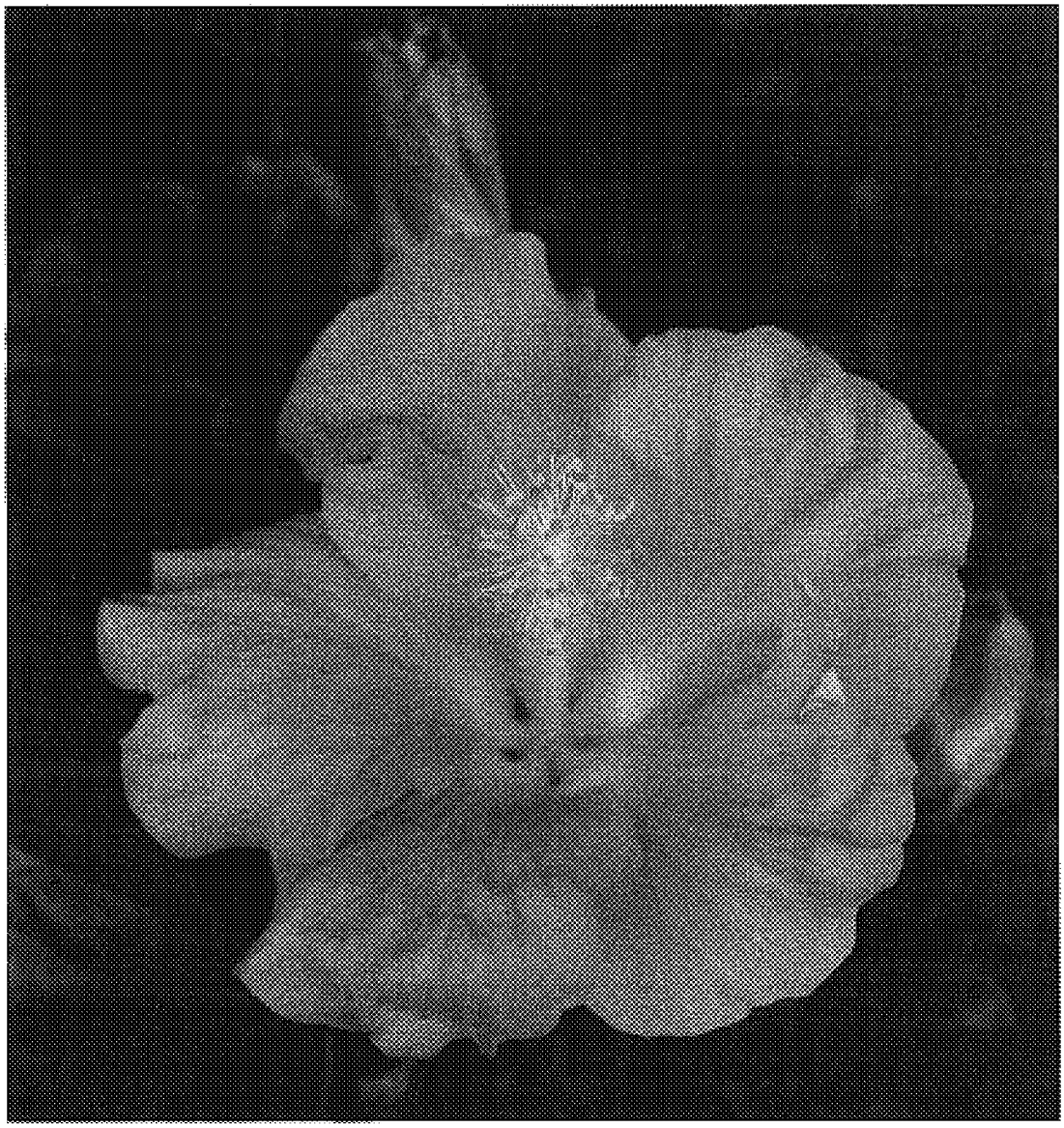

* * * * *